Figure 1:
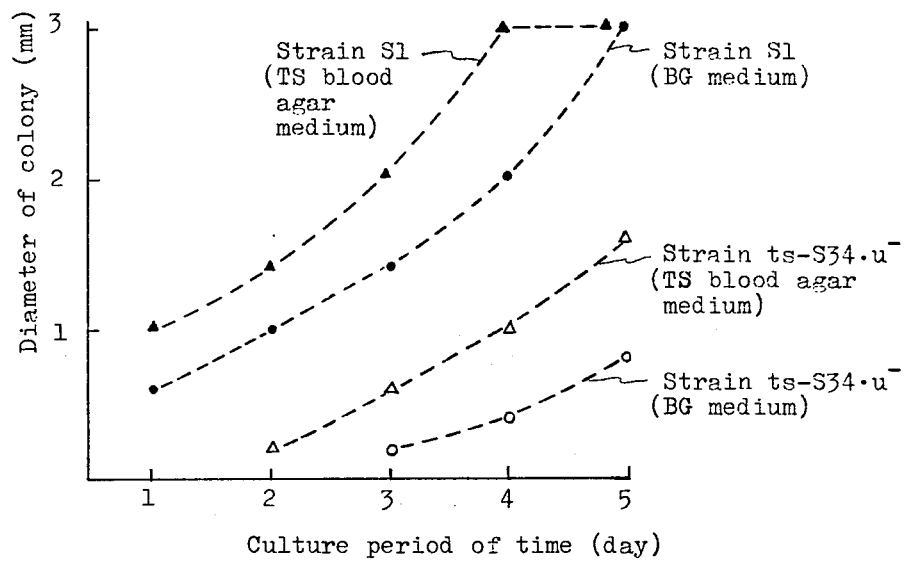

United States Patent [19]

Shimizu

[11] 4,456,588
[45] Jun. 26, 1984

[54] METHOD OF THE PREPARATION OF IMPROVED MUTANT STRAIN OF *BORDETELLA BRONCHISEPTICA* USEFUL AS LIVE ATTENUATED VACCINE FOR PROPHLAXIS OF *B. BRONCHISEPTICA* INFECTION

[75] Inventor: Takeshi Shimizu, K2-2, 5, Hitsujigaoka, Toyohira-ku, Sapporo-shi, Hokkaido, Japan

[73] Assignees: Juridical Foundation The Chemo-Sero-Therapeutic Research Institute, Nippon Vaccine Co., Ltd., Shimizu; Takeshi Shimizu, Sapporo, both of Japan

[21] Appl. No.: 400,363

[22] Filed: Jul. 21, 1982

[30] Foreign Application Priority Data

Aug. 10, 1981 [JP] Japan ................................. 56-125530

[51] Int. Cl.³ ...................... A61K 39/10; C12N 15/00; C12N 1/00
[52] U.S. Cl. .................................. 424/92; 435/172.1; 435/253

[58] Field of Search ................... 424/92; 435/253, 172

[56] References Cited

U.S. PATENT DOCUMENTS 4,225,583  9/1980  Switzer et al. ........................ 424/92

OTHER PUBLICATIONS

Shimizu, Ti, Infection and Immunity, vol. 22, pp. 318–321, 1978.

*Primary Examiner*—Blondel Hazel
*Attorney, Agent, or Firm*—Wegner & Bretschneider

[57] ABSTRACT

A method for the preparation of a new mutant strain of *Bordetella bronchiseptica* having a plural of hereditary chromosomal markers of at least temperature-sensitivity and urease negative, more particularly a phase I mutant strain of *B. bronchiseptica* having excellent immunity and high safety, which is useful for the preparation of a live attenuated vaccine for prophylaxis of *B. bronchiseptica* infection, and also a live attenuated vaccine prepared therefrom, and use thereof.

10 Claims, 1 Drawing Figure

METHOD OF THE PREPARATION OF IMPROVED MUTANT STRAIN OF *BORDETELLA BRONCHISEPTICA* USEFUL AS LIVE ATTENUATED VACCINE FOR PROPHLAXIS OF *B. BRONCHISEPTICA* INFECTION

The present invention relates to a method for the preparation of a new mutant strain of *Bordetella bronchiseptica*, more particularly a phase I mutant strain of *B. bronchiseptica* having excellent immunity and high safety, which is useful for the preparation of a live attenuated vaccine for prophylaxis of *B. bronchiseptica* infection, and also a live attenuated vaccine prepared therefrom and use thereof.

*Bordetella bronchiseptica* is known to cause respiratory diseases in various animals, such as swine, dogs, rabbits, guinea pigs, or mice, particularly to cause infectious atrophic rhinitis of swine infant which induces nasal turbinate atrophy and results in growth retardation and lowering of feed efficiency. This is a big problem in livestock industry. There have recently been proposed killed vaccines for prophylaxis of infectious atrophic rhinitis of swine, but they are still unsatisfactory.

The present inventor had developed a mutant strain of *B. bronchiseptica* useful for the preparation of a live attenuated vaccine for prophylaxis of *B. bronchiseptica* infection, which has been derived from a wild strain of *B. bronchiseptica*, particularly a wild virulent strain (hereinafter, referred to as "strain S1") isolated from the nasal cavity of swine suffered from infectious atrophic rhinitis (cf. Japanese Patent Publication No. 47612/1980 and Infection and Immunity, Vol. 22, No. 2, pages 318–321, Nov. 1978). That is, it has been succeeded to obtain a temperature-sensitive (ts) mutant strain of *B. bronchiseptica* which can grow at 32° C. but can not grow at 34°–37° C. or above (hereinafter, referred to as "strain ts-S34") by the steps of culturing the strain S1 on a blood agar medium, treating a saline suspension of the resulting organism with nitrosoguanidine, repeating centrifuge of the saline suspension, washing it, culturing the cells on a blood agar medium, and then collecting the temperature-sensitive mutant strain by using the replica method.

The strain ts-S34 thus obtained has excellent immunogenicity with slight virulence and is useful for the preparation of a live attenuated vaccine for prophylaxis of *B. bronchiseptica* infection. However, it has still a little bit problem in safety in order to use as a live vaccine in commercial scale and is still insufficient in discrimination in vitro from wild and/or virulent strains or in approval in case of the industrial production or field application.

In order to obtain another mutant strain of *B. bronchiseptica* having improved properties, the present inventor has extensively tried to give the strain other hereditary markers in addition to the temperature-sensitivity as in the strain ts-S34, by which the mutant strain can more easily be distinguished from wild and virulent strains and can be approved as a live vaccine with higher assurance, which are advantageous for industrial production of a live attenuated vaccine. As a result, it has been found that the desired improved mutant strain suitable for the production of a live attenuated vaccine for prophylaxis of *B. bronchiseptica* infection can be obtained by applying a mutagen, preferably a plural of mutagen, to a saline suspension of a strain of *B. bronchiseptica*, isolating a mutant strain having a plural of hereditary markers, culturing the isolated mutant strain on a blood agar medium for a long period of time, picking up a cell grown with a small colony, culturing the cell on a blood agar medium, and repeating the picking up of a cell and culture thereof.

An object of the present invention is to provide a method for the production of a new mutant strain of *B. bronchiseptica* suitable for the production of a live attenuated vaccine for prophylaxis of *B. bronchiseptica* infection. Another object of the invention is to provide a mutant strain of *B. bronchiseptica* having a plural of hereditary markers, particularly temperature-sensitivity and urease negative, which are effective for discrimination from wild and/or virulent strains and for approval as a live vaccine. A further object of the invention is to provide a live attenuated vaccine for prophylaxis of *B. bronchiseptica* infection, particularly infectious atrophic rhinitis in swine. These and other objects and advantages of the present invention will be apparent to persons skilled in the art from the following description.

According to the present invention, the mutant strain having a plural of hereditary markers can be obtained by applying a mutagen, preferably a plural of mutagen, to a saline suspension of strain of *B. bronchiseptica*, preferably organisms in logarithmic growth phase which are obtained by culturing the bacteria on a blood agar medium for about 6 to 24 hours, centrifuging the saline suspension thus treated a few or several times, washing it, culturing the resulting strain on a blood agar medium and then collecting mutant strain having at least temperature-sensitivity and urease negative (hereinafter, referred to as "strain ts-34.u$^-$") from the colonies. However, the isolated strain is a phase III organism which looses the specific antigen, i.e. capsular antigen and is anhemolytic and hence is not suitable for producing a live vaccine. Accordingly, this phase II organism is cultured on a blood agar medium for a long period of time, and a cell grown with comparatively small colony is picked up and used as a next seed culture, i.e. the cell is cultured on a blood agar medium. After repeating the procedure of picking up a cell and culturing thereof, there can be obtained the desired phase I organism of strain ts-S34.u$^-$ having completely capsular antigen and being hemolytic, via a weakly hemolytic phase II organism.

The starting strain used in the above method may be a wild strain of *B. bronchiseptica* (e.g. strain S1), or may be the strain ts-S34 having temperature-sensitivity which is produced by the method disclosed in the above-mentioned literatures. When a wild strain is used as the starting strain, the strain is converted into a mutant strain having temperature-sensitivity by applying thereto a mutagen as disclosed in the above-mentioned literature, and then the urease negative property is given to the mutant strain by applying thereto a mutagen. Alternatively, the starting wild strain is firstly converted into a mutant strain having urease negative property by applying thereto a mutagen, and then the temperature-sensitivity is given to the mutant strain likewise. Practical viewpoint, it is preferable to use the strain ts-S34 as the starting strain.

The phase I strain ts-S34.u$^-$ thus obtained has, as mentioned hereinafter, a plural of hereditary chromosomal markers such as urease negative in additon to temperature-sensitivity, and further growth retardation (e.g. formation of colony on a blood agar medium takes about 3 to 4 days). and further, the strain has completely capsular antigen which is essential as a live vaccine and has high safety and higher immunogenicity than the strain ts-S34. Accordingly, this phase I strain ts-S34.u⁻ is particularly useful for the production of a live attenuated vaccine for prophylaxis of *B. bronchiseptica* infection.

The method for the production of the phase I strain ts-34.u⁻ is explained in more detail (wherein for explanation purpose, the strain ts-S34 is used as the starting strain).

(1) Production of phase III strain ts-S34.u⁻ from strain ts-S34

Strain ts-S34 obtained by the method disclosed in Japanese Patent Publication No. 47612/1980 and Infection & Immunity as mentioned above is used. The strain ts-S34 is cultured on a blood agar medium (component: trypticase soy agar medium (BBL), i.e. soybean-casein digest agar medium disclosed in U.S. Pharmacopeia, XX, July 1, 1980, page 875, to which 10% defibrinated sheep blood is added) (hereinafter, referred to as "TS blood agar medium") at 32° C. overnight, and the resulting cells are taken into an appropriate buffered saline solution, e.g. a phosphate buffered saline solution (pH 7.0), and to the resulting saline suspension of cells in logarithmic growth phase is applied a mutagen, preferably a plural of mutagen.

The mutagen includes the conventional means for mutating microorganisms, for example treatment with various mating agents such as nitrosoguanidine (e.g. N-methyl-N'-nitro-N-nitrosoguanidine), nitrous acid, 2-aminopurine, 5-bromouracil, etc., and ultraviolet irradiation or radiation irradiation. These means may be used alone, but preferably be used in combination of two or more thereof in order to obtain the desired mutant strain having a plural of hereditary markers more effectively. Preferred combination is a combination of the treatment with nitrosoguanidine and ultraviolet irradiation.

The mutant strain thus obtained is isolated by centrifuge, washed, and then cultured on a blood agar medium at 32° C. for 3 days. The cells in grown colony are subjected to urease test and the strain having urease negative is collected to give strain ts-S34.u⁻, which is phase III organism.

(2) Production of phase I organism from phase III organism

The present inventor has aimed at the fact that phase I organism of *B. bronchiseptica* grows with a small colony and is strongly hemolytic, but on the other hand, phase III organism grows with a large colony and is anhemolytic, and has found a method for converting the phase III organism into the phase I organism.

The phase III strain ts-S34.u⁻ is cultured on a blood agar medium (component: Bordet-Gengou medium (Difco) with 10% defibrinated sheep blood, cf. "Saikingaku Jisshu Teiyo" (Manual of Practice in Bacteriology) 5th Ed. (1976) in Japan, page 79 and "Manual of Clinical Microbiology" issued by American Soc. for Microbiology, 2nd Ed. (1974), pages 894–895) (hereinafter, referred to as "BG medium"), at 32° C. for 3 days or longer, usually 3 to 6 days, and from comparatively small colonies a cell being preferably hemolytic even a little is picked up and is cultured on the same medium. This procedure of picking up a cell and culture thereof is repeated twice or more times, usually 2 to 10 times, by which the desired phase I organism being strongly hemolytic is isolated via phase II organism being weakly hemolytic. This phase I strain ts-s34.u⁻ was deposited to Fermentation Research Institute (FRI), Japan as FERM P-6099.

The phase I strain ts-S34.u⁻ has the following characteristics.

(1) Biological characteristics (a) Temperature-sensitivity

This strain grows at 32° C. but does not grow at 34° to 37° C. or above like the strain ts-S34.

(b) Urease test

The urease test was carried out by a usual urease test using a urease test broth (cf. the above-mentioned "Manual of Clinical Microbiology", 2nd Ed. (1974), pages 923–924). The test was done on various bacteria, such as several subcultures of phase I organism strain ts-S34, wild strain S1, another wild strain A-19 which was derived from swine suffered from infectious atrophic rhinitis, a strain of *Alcaligenes faecalis* which has very similar biological characteristics to those of wild *B. bronchiseptica* except urease negative (cf. Cowan and Steel's, Manual for the Identification of Medical Bacteria, 2nd Ed. 1974), and *E. coli* (same bacteria were used in other tests mentioned hereinafter). The results are shown in Table 1.

TABLE 1

| Strains | 2 hours* | 7 days |
|---|---|---|
| ts-S34.u⁻ phase I | | |
| Original | − | − |
| Subculture of 5 passages | − | − |
| Subculture of 7 passages | − | − |
| Subculture of 10 passages | − | − |
| Subculture of 20 passages | − | − |
| ts-S34.u⁻ phase II | − | − |
| ts-S34.u⁻ phase III | − | − |
| ts-S34 | − | − |
| S1 | − | − |
| A-19 | − | − |
| *Alcaligenes faecalis* | − | − |
| *E. coli* | − | − |

*Usual period of time for evaluation

As is clear from the above test results, the phase I strain ts-S34.u⁻ is urease negative, and this hereditary characteristic is very stable.

(c) Colony growing rate

Colony growing rates of various bacteria were compared in terms of growth on two kinds of plate media.

By using TS blood agar medium on which bacteria grow well and BG medium on which bacteria grow less, bacteria were cultured at 32° C. for 5 days, and the diameter of each colony was measured every day. The results are shown in the accompanying FIG. 1. As is clear from the results, until the diameter of colony became more than 0.5 mm, the phase I strain ts-S34.u⁻ took 3 to 5 days, which means that this strain is late colony-growing in comparison with the wild phase I strain S1.

Besides, by using KCN medium (cf. the above-mentioned "Manual of Clinical Microbiology", 2nd Ed. (1974), page 915) and Simmons citrate agar medium (cf. the above-mentioned "Manual of Clinical Microbiology", 2nd Ed. (1974), page 898), the bacteria were cultered at 32° C. for several days. The results are shown in Tables 2 and 3, respectively.

TABLE 2

| | Growth in KCN medium | | |
|---|---|---|---|
| | Culture period of time | | |
| Strains | 2 days* | 3 days | 4 days |
| ts-S34.u⁻ phase I | | | |

TABLE 2-continued

Growth in KCN medium

| Strains | Culture period of time | | |
|---|---|---|---|
| | 2 days* | 3 days | 4 days |
| Original | − | ± | + |
| Subculture of 5 passages | − | ± | + |
| Subculture of 7 passages | − | ± | + |
| Subculture of 10 passages | − | ± | + |
| Subculture of 20 passages | − | ± | + |
| ts-S34.u⁻ phase II | + | + | + |
| ts-S34.u⁻ phase III | + | + | + |
| ts-S34 | + | + | + |
| S1 | + | + | + |
| A-19 | + | + | + |
| Alcaligenes faecalis | + | + | + |
| E. coli | − | − | − |

*Usual period of time for evaluation

TABLE 3

Growth on Simmons citrate agar medium

| Strains | Culture period of time | | |
|---|---|---|---|
| | 1 day | 4 days* | 7 days |
| ts-S34.u⁻ phase I | | | |
| Original | − | − | + |
| Subculture of 5 passages | − | − | + |
| Subculture of 7 passages | − | − | + |
| Subculture of 10 passages | − | + | + |
| Subculture of 20 passages | − | + | + |
| ts-S34.u⁻ phase II | − | + | + |
| ts-S34.u⁻ phase III | − | + | + |
| ts-S34 | − | − | + |
| S1 | ± | + | + |
| A-19 | + | + | + |
| Alcaligenes faecalis | + | + | + |
| E. coli | − | − | − |

*Usual period of time for evaluation

As is clear from the above results, the present phase I strain ts-S34.u⁻ was negative at usual culture period of time for evaluation and became positive at a longer culture period of time, which means that the strain is late colony-growing.

Other biological characteristics of the present phase I strain ts-S34.u⁻ are the same as those of strain S1 and strain ts-S34.

(2) Antigenic characteristic

Anti-S1 hyperimmune rabbit serum and anti-ts-S34.u⁻ hyperimmune pig serum, which were prepared by highly immunizing anti-rabbit serum and anti-pig serum with phase I strain S1 phase I strain ts-S34.u⁻ respectively were subjected to an agglutination test in vitro by using as an antigen phase I strain S1, phase I strain ts-S34.u⁻, a commercially available antigen for atrophic rhinitis (AR antigen 'Hokken'), and Alcaligenes faecalis IAM 1473 (cf. T. Shimizu, Atrophic Rhinitis, 3. Serodiagnosis, in Pig Pathology issued by Kindai Shuppan, Tokyo, Japan in 1977). The results are shown in Table 4.

TABLE 4

Agglutinability against anti-S1 hyperimmune rabbit serum and anti-ts-S34.u⁻ hyperimmune pig serum

| Antigen | Anti-S1-hyperimmune rabbit serum | Anti-ts-S34.u⁻-hyperimmune pig serum |
|---|---|---|
| Strain S1 | 20,480 | 20,480 |
| Strain ts-S34.u⁻ | 20,480 | 20,480 |
| AR antigen 'Hokken' | 20,480 | 20,480 |
| Alcaligenes faecalis | <10 | <10 |

[Remark]: The antigens were all phase I organisms.

As is clear from the above results, three antigens including the phase I strain ts-S34.u⁻ all showed an agglutinin titer of 20,480 times, and hence, the phase I strain ts-S34.u⁻ has the same antigenicity as the wild phase I strain S1. On the contrary, Alcaligenes faecalis having very similar biological characteristics to the phase I strain ts-S34.u⁻ showed an agglutinin titer of less than 10 times, which means that Alcaligenes faecalis is quite different from the phase I strain ts-S34.u⁻ in antigenicity.

(3) Test of prophylactic value and safety of live attenuated vaccine prepared from the phase I strain ts-S34.u⁻

Prophylactic value of a live vaccine prepared from the phase I strain ts-S34.u⁻ was tested by the following method using guinea pigs.

Guinea pigs of Hartley strain, weighing about 300 g (22 animals) were divided into immunized group (12 animals) and control group (10 animals).

Phase I strain ts-S34.u⁻ was cultured on BG medium at 32° C. for 2 days and the cells were taken into phosphate buffered saline solution (pH 7.0). The cell suspension thus obtained (each 0.2 ml) was inoculated into both nasal cavities of guinea pigs of the group to be immunized (total 0.4 ml, $6 \times 10^8$ organisms). At 4 week after immunization, all guinea pigs of both immunized group and control group were challenged with virulent phase I strain S1 of B. bronchiseptica by inoculating a cell suspension of the bacteria (each 0.2 ml) into both nasal cavities of guinea pigs (total 0.4 ml), said cell suspension being prepared by culturing the bacteria on BG medium at 37° C. for one day and taking the grown bacteria cells into phosphate buffered saline solution (pH 7.0). The inoculation amount for challenge was totally $1.32 \times 10^{10}$ organisms [i.e. $15,000 \times LD_{50}$ (50% lethal dose). The animals were observed for 5 weeks after challenge. The results are shown in Table 5.

TABLE 5

| Guinea pigs | Number of died animals/number of total animals | Date of death |
|---|---|---|
| Immunized group | 0/12 | ⊚ ⊚ ⊚ ⊚ ⊚ ⊚<br>⊚ ⊚ ⊚ ⊚ ⊚ ⊚ |
| Control group | 10/10 | ● ● ● ● ● ●<br>1 2 3 5 6<br>● ● ● ● ●<br>7 8 10 12 14<br>● ● ● ● ● |

* ⊚ : Survived
● : Died (number means date of death)

As is clear from the above results, in the immunized group which were immunized with the live vaccine of the phase I strain ts-S34.u⁻, all 12 animals were survived without manifesting clinical symptoms, and further no pathological change was observed by autopsy at 5 weeks after challenge. On the contrary, in the unvaccined control group, all 10 animals were died of septicemia with difficulty in breathing within 14 days after challenge.

Thus, the present phase I strain ts-S34.u⁻ shows excellent immunity against B. bronchiseptica infection with high safety, i.e. without any clinical symptoms.

(4) Assay of heatlabile toxin

It is considered that the heatlabile toxin (hereinafter referred to as "HLT") of B. bronchiseptica participates the nasal turbine atrophy in swine infected with the bacteria. Accordingly, it is important to eliminate the undesirable side effect due to the HLT in the live attenuated vaccine for infectious atrophic rhinitis.

The side effect due to the HLT in various bacteria was assayed by using guinea pigs. The test bacteria were the present phase I strain ts-S34.u⁻ and further strain ts-S34, strain S1, *Alcaligenes faecalis* IAM 1473 and *E. coli* B 41.

Each test strain (phase I organism) was cultured on TS medium at 32° C. for 2 days and the cells were harvested in distilled water (5 ml). The resulting cell suspension of each test bacteria ($5 \times 10^{11}$ organisms/ml) was sonicated with a sonicator (Sonifer model 200, 150 W) at 20 KHz for 15 minutes, and the mixture was centrifuged under cooling at 4° C. and at 15,000 r.p.m. for 30 minutes and then filtered with 0.3 μm Millipore filter. A serial two-fold dilution of the resulting mixture was made with a physiological saline. One tenth ml of each solution was inoculated intracutaneously to guinea pigs of Hartley strain, weighing about 300 g, and there was determined the maximum fold dilution, at which necrotic lesions appeared at one day after inoculation. The results are shown in Table 6.

TABLE 6

| Strains | Maximum fold dilution |
| --- | --- |
| Strain ts-S34.u⁻ | × 2 |
| Strain ts-S34 | × 4 |
| *Alcaligenes faecalis* IAM 1473 | × 1 |
| Strain S1 | × 64 |
| *E. coli* B 41 | × 2 |

As is clear from the above results, the present phase I strain ts-S34.u⁻ has a very low HLT and is about half of that of the strain ts-S34. This fact indicates that the present phase I strain ts-S34.u⁻ is very safe as a live vaccine under taking into consideration together with no clinical symptoms in the above-mentioned test for prophylactic value.

Thus, the phase I strain ts-S34.u⁻ of the present invention has specific hereditary chromosomal markers and is extremely excellent in immunogenecity and also in safety, and hence, it is very useful for the production of a live attenuated vaccine for prophylaxis of *B. bronchiseptica* infection.

The live attenuated vaccine for prophylaxis of *B. bronchiseptica* infection can be produced by a conventional method from the present phase I strain ts-S34.u⁻. For example, the phase I strain ts-S34.u⁻ is cultured on a blood agar medium (e.g. BG medium) at 32° C. to grow sufficiently, and the grown cells are harvested in a phosphate buffered saline solution (pH 7.0) to prepare a cell suspension. The suspension is mixed with a usual drying protecting agent, e.g. a mixture of 10% skim milk and 5% yeast extract (the cell suspension:the mixture=1:1 by volume) and packed dividedly in vials, followed by lyophilization. The product is restored with a phosphate buffered saline (pH 7.0) when used, and the restored solution is administered into nasal cavity of animals by pouring or spraying.

The vaccine is usually administered to the animal in an amount of more than $10^4$ organisms, preferably $10^5$ to $10^9$ organisms.

The present invention is illustrated by the following Examples but is not limited thereto.

EXAMPLE 1

(1) Preparation of strain ts-S34.u⁻ from strain ts-S34

Strain ts-S34 of *B. bronchiseptica* is inoculated on a blood agar medium (TS blood agar medium) and cultured at 32° C. for one day. The grown cells are harvested in a phosphate buffered saline (pH 7.0) to give a cell suspension. To the cell suspension (4 ml) is added N-methyl-N'-nitro-N-nitrosoguanidine in a final concentration of 1,000 μg/ml, and the mixture is incubated with shaking at 32° C. for one hour. The culture solution is then irradiated with ultraviolet ray (distance: 10 cm, time: 4 seconds). The resulting solution is centrifuged at 3,000 r.p.m. for 15 minutes (repeated three times) and then is washed with the same phosphate buffered saline as above. The resulting cells are resuspended in the same phosphate buffered saline and are cultured on the same blood agar medium as above at 32° C. for 3 days. From the resulting colonies, urease negative strain is collected in accordance with urease test to give phase III strain ts-S34.u⁻.

(2) Preparation of phase I organism from phase III organism

The phase III strain ts-S34.u⁻ is suspended in a phosphate buffered saline (pH 7.0), and the diluted cell suspension is cultured on a blood agar medium (BG medium) at 32° C. for 3 days or longer. From a comparatively small colony produced after more than 3 days, a cell is picked up and is grown on the same medium as above. The culture thus obtained is cultured again and the cell is picked up in the same manner as above. After repeating ten times the above procedure, there is obtained phase I organism grown with a small colony which shows strong hemolytic property, via phase II organism having weak hemolytic property.

EXAMPLE 2

In the same manner as described in Example 1, (1) except that the cell suspension to which is added N-methyl-N'-nitro-N-nitrosoguanidine in a final concentration of 1,000 μg/ml is incubated with shaking at 32° C. for one hour instead of the treatment with nitrosoguanidine and ultraviolet irradiation, there is obtained phase III strain ts-S34.u⁻. The organism thus obtained is treated in the same manner as described in Example 1, (2) except that the procedure of culture and picking up the cell is repeated four times to give phase I strain ts-S34.u⁻.

EXAMPLE 3

In the same manner as described in Example 1, (1) except that the cell suspension is irradiated with ultraviolet ray (distance: 20 cm, time: 4 seconds) instead of the treatment with nitrosoguanidine and ultraviolet irradiation, there is obtained phase III strain ts-S34.u⁻. The organism thus obtained is treated in the same manner as described in Example 1, (2) except that the procedure of culture and picking up the cell is repeated four times to give phase I strain ts-S34.u⁻.

EXAMPLE 4

The phase I strain ts-S34.u⁻ of *B. bronchiseptica* obtained in Example 1 is inoculated on BG medium (pH 6.8, added with 10% defibrinated sheep blood) and cultured at 32° C. for 2 days. The grown cells are collected and suspended in a sterilized phosphate buffered saline (pH 7.0) in a concentration of $1.5 \times 10^9$ organisms./ml. The cell suspension is admixed well with an equiamount of a drying protecting agent (a mixture of 10% skim milk and 5% yeast extract, which is sterilized at 110° C. for 10 minutes) to give a final bulk. This bulk (each 2 ml) is poured into 10 ml vials, which are lyophilized and sealed under reduced pressure to give a little vaccine (lyophilized). When the product is kept at a dark place at 2°-5° C., the properties thereof are very stably kept. Besides, this product can easily be dissolved in a solvent, e.g. a sterilized phosphate buffered saline (pH 7.0) and shows uniform properties. When the product is dissolved in a solvent (10 ml), the solution contains sufficiently satisfactory amount of live bacteria, more than $10^8$ organisms/ml.

Test I:

The phase I strain ts-S34.u$^-$ obtained in Example 1 was subjected to safety test using HPCD pigs. There were used eight HPCD young pigs, 6 days age which were negative in B. bronchiseptica antibody. The pigs were divided into four groups, wherein in three groups the bacteria was inoculated in an amount of $6.2 \times 10^7$, $6.2 \times 10^8$ and $6.2 \times 10^9$ organisms, respectively, and in another one group no bacteria was inoculated (each group: two animals). The bacterial cell suspension (each 1.0 ml) was inoculated into nasal cavity of each animal. After observing for 12 weeks, the animals were subjected to autopsy. During the observation, any abnormal symptoms in activity, appetite, etc. were not observed in all animals of the vaccinated and unvaccinated groups. Besides, any abnormal symptoms were not shown on the macroscopic and microscopic observations. Thus, the mutant strain of the present invention is safe for swine.

Test II:

The live vaccine obtained in Example 4 was dissolved in a sterilized phosphate buffered saline and diluted with the same solution in a series of 10-fold dilution. Immunogenicity of the vaccine in a concentration of about $10^4$, $10^6$ and $10^8$ organisms/ml was tested by using HPCD pigs.

Eight HPCD young pigs, 6 days age which were negative in B. bronchiseptica antibody were divided into four groups, wherein in three groups the vaccine was inoculated in an amount of $6.2 \times 10^4$, $6.2 \times 10^6$ and $6.2 \times 10^8$ organisms, respectively, and in another group no vaccine was inoculated (each group: two animals). The diluted vaccine was inoculated into nasal cavity of each animal in an amount as mentioned above. Three weeks after the inoculation, all animals were challenged with a strongly virulent wild strain S1 of B. bronchiseptica by administering the strain into nasal cavity in an amount of $2.5 \times 10^7$ organisms per animal. Ten weeks after the challenge, the animals were subjected to autopsy. During the observation period from the challenge till the autopsy, all animals of the vaccinated groups showed no abnormal symptoms in the general observation such as activity, appetite, etc. and also in the clinical symptoms. The turbinate atrophy was also negative in cases of animals inoculated with $6.2 \times 10^6$ and $6.2 \times 10^8$ organisms, while one animal inoculated with $6.2 \times 10^4$ organisms showed alight pneumonia and slight turbinate atrophy. On the contrary, in the unvaccinated group, the animals showed clinical symptoms such as eye patch and sneezing, and the feed efficiency was lower effective, and further, turbinate atrophy was observed by the autopsy. It was confirmed from the above data that the vaccine of the present invention is effective.

Test III:

The phase I strain ts-S34.u$^-$ was tested using HPCD pigs whether the virulence was reproduced. The live strain was inoculated in an amount of $6.2 \times 10^8$ organisms into nasal cavity of HPCD pigs, 6 days age. After observing for 11 weeks, the nasal cavity was swept with a sterilized cotton stick and the swept material was suspended into a phosphate buffered saline (pH 7.0) (2 ml). One ml of the suspension was inoculated to another pigs and another one ml was cultured in order to identify the bacteria and also to test the properties of the bacteria. The procedure was repeated three times (two pigs were used in each procedure). All animals in the first, second and third procedure and also in control group (not inoculated with the bacteria) showed no abnormal symptoms such as activity, appetite, etc. and no abnormal symptoms on the macroscopic and microscopic observations. It was confirmed from the above data that the strain of the present invention does not reproduce the virulence and is very safeful.

What is claimed is:

1. A method for the preparation of a strain of Bordetella bronchiseptica having hereditary chromosomal markers of being temperature-sensitive and urease negative and which is useful in the production of a live vaccine for prophylaxis of Bordetella bronchiseptica infection, which comprises subjecting a strain of Bordetella bronchiseptica to a conventional means for mutating microorganisms to obtain a strain having the hereditary markers of being temperature-sensitive in that it can grow at 32° C. but not above 34° C. and urease negative, culturing the strain on a blood agar medium, picking up a cell grown with a comparatively small colony, culturing the cell on a blood agar medium, and repeating the procedure of picking up a cell and culture thereof to convert it into phase I organisms which has completely capsular antigen and is hemolytic.

2. A method according to claim 1, wherein the means for mutating microorganisms is a combination of treatment with nitrosoguanidine and ultraviolet irradiation.

3. A method according to claim 1, wherein the procedure of picking up a cell and the culture thereof is repeated at least twice.

4. A method according to claim 3, wherein the procedure of picking up a cell and the culture thereof is repeated from 2 to 10 times.

5. A method according to claim 1, wherein the starting strain of Bordetella bronchiseptica is a strain of Bordetella bronchiseptica which can grow at 32° C. but not above 34° C.

6. A method according to claim 1, wherein the starting strain of Bordetella bronchiseptica is a strain of Bordetella bronchiseptica isolated from the nasal cavity of swine suffering from infectious atropic rhinitis.

7. A method for the prophylaxis of Bordetella bronchiseptica infection, which comprises administering to an animal an effective amount of a live attenuated vaccine prepared with a phase I strain ts-S34.u$^-$ of Bordetella bronchiseptica having hereditary chromosomal markers of being temperature-sensitive in that it can grow at 32° C. but not above 34° C. and urease negative.

8. A method according to claim 1, wherein the live attenuated vaccine is administered to the animal via its nasal cavity.

9. A live attenuated vaccine for prophylaxis of Bordetella bronchiseptica infection, which comprises phase I Bordetalla bronchiseptica strain ts-S34.u$^-$ having hereditary chromosomal markers of being temperature-sensitive in that it can grow at 32° C. but not above 34° C. and urease negative, and a carrier therefor.

10. A biologically pure culture of Bordetella bronchiseptica strain ts-S34.u$^-$ having the hereditary chromosomal markers of being temperature-sensitive in that it can grow at 32° C. but not above 34° C. and urease negative.

* * * * *